United States Patent [19]
Kiffe

[11] Patent Number: 4,773,258
[45] Date of Patent: Sep. 27, 1988

[54] ELECTRONIC MEASURING GAUGE FOR HARDNESS TESTER

[76] Inventor: Horst-Gregor Kiffe, Vogelbeerweg 19, 7730 VS-Villingen, Fed. Rep. of Germany

[21] Appl. No.: 46,389

[22] Filed: May 6, 1987

[30] Foreign Application Priority Data

May 9, 1986 [DE] Fed. Rep. of Germany ....... 3615696

[51] Int. Cl.⁴ ............................................. G01N 3/44
[52] U.S. Cl. ............................................ 73/81; 73/83
[58] Field of Search .......................... 73/81, 78, 85, 83

[56] References Cited

U.S. PATENT DOCUMENTS

| | | | |
|---|---|---|---|
| 4,118,975 | 10/1978 | Iwasaki | 73/81 |
| 4,159,640 | 7/1979 | Lévéque et al. | 73/81 |
| 4,246,777 | 1/1981 | Birner et al. | 73/83 |
| 4,262,525 | 4/1981 | Ernst | 73/81 |
| 4,304,123 | 12/1981 | Aschinger et al. | 73/81 |
| 4,450,713 | 5/1984 | Arimatsu | 73/81 |
| 4,691,559 | 9/1987 | Fischer | 73/81 |

*Primary Examiner*—Tom Noland
*Attorney, Agent, or Firm*—Leonard Bloom

[57] ABSTRACT

A measuring gauge which may be retrofitted to existing hardness testers to replace existing mechanical measuring gauges and which can be installed with minimal assembly expense. The gauge includes a movable feeler pin, a movable tracking member, and a resilient coupling member for securing the pin to the tracking member, whereby the movable tracking member tracks the movement of the feeler pin. An electrical sensor senses the movement of the movable tracking member. An amplifier amplifies the sensed movement of the tracking member and a digital display displays the sensed movement of the tracking member.

22 Claims, 4 Drawing Sheets

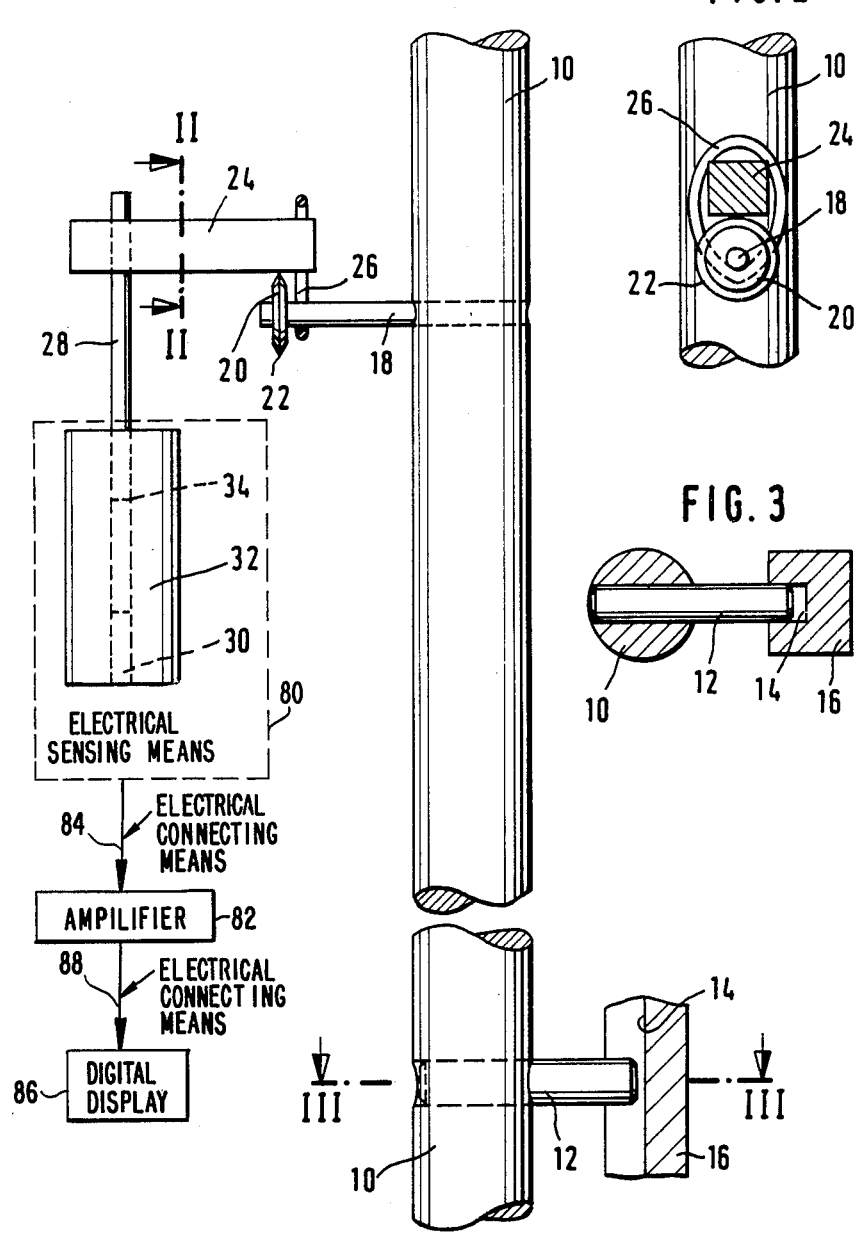

ELECTRONIC MEASURING GAUGE FOR HARDNESS TESTER

FIELD OF THE INVENTION

The invention concerns an electronic digital measuring gauge for a hardness tester.

BACKGROUND OF THE INVENTION

The indicators of measuring gauges with mechanical drives are fundamentally inexact because of the presence of parasitic frictional forces and the play in sprocket gears. Besides that, an up-to-date technical further improvement of the measurements through the use of mechanical measuring gauges is problematical and not possible.

Because of these reasons, new or already at-hand hardness testers have lately been outfitted (retrofitted) at great cost with electronic measurement systems. This requires not only a great production but also assembly expense in order to outfit an already existing apparatus with an electronic measurement system.

There is however, the need to modernize, make usable and to provide a suitable electronic measuring gauge which may be retrofitted for the large number of hardness testers, already in service for years, without such a large production an assembly expense.

SUMMARY OF THE INVENTION

The invention therefore has the task to create an electronic digital measuring gauge for hardness testers which corresponds to the finished dimensions of a mechanical measuring gauge and which, therefore, allows for the direct exchange (retrofit) of a mechanical measuring gauge with an electronic measuring gauge with minimum assembly expense.

In order to provide for the relatively complicated electronic measurement system in the limited space provided for the measuring gauge, the measurer of the measuring path must be kept relatively small in its dimensions and measure very accurately. This is possible with the prototype of the invention. An accurate measurement assumes an exact, in other words relatively long, drive of the feeler pin. Opposed to this, the feeler pin cannot be driven concentric through the inductive measurement coil. Correspondingly, the path measurer is located parallel to the feeler pin, and the control core, for example a core made from ferrite or other similar material, is situated concentric in the measurement coil which can also be formed as a coil system, and is thereby coupled with the feeler pin through the crane beam.

With an appropriate development of the invention, the measuring rod consists of ceramic material and the ferrite core, serving as control core, is embedded in the ceramic material.

In order to achieve a good measuring accuracy it is important, except in the case of known measuring gauges utilizing turning-prevention of the feeler pin and thereby of the measuring rod, that the control core be positioned exactly in the center of the core of the winding. An error resulting from an imperfect positioning could be made ineffectual by making the inner diameter of the measurement coil so large that the turning play position, and drive errors do not influence the measurement. This would, however, be accomplished at the expense of the finished size of the measuring gauge.

In accordance with the teachings of the present invention, an electronic digital measuring gauge which may be retrofitted to a hardness tester is disclosed. This gauge includes a movable feeler pin and a movable tracking member. A resilient, mechanical coupling means is positioned between the feeler pin and the movable tracking member. This coupling means secures the feeler pin and the movable tracking member to one another, wherein the movable tracking member tracks the movement of the feeler pin. An electrical sensing means or sensor is provided for electrically sensing the movement of the movable tracking member. An amplifier amplifies the electrically sensed movement of the tracking member. Means is provided for electrically connecting the amplifier and the sensing means. This means conducts the electrically sensed movement of the tracking member from the electrical sensing means to the amplifier. A digital display digitally displays the electrically sensed movement of the tracking member. Finally, means is provided for electrically connecting the amplifier and the digital display. This means conducts the electrically sensed movement from the amplifier to the digital display. Preferably, the feeler pin and the tracking member are positioned on respective longitudinal axes.

In further accordance with the teachings of the present invention, there is disclosed an electronic digital measuring gauge for a hardness tester. This gauge includes a housing. A movable feeler pin is positioned on a first longitudinal axis. This pin is further disposed through the housing and extends outwardly therefrom. A crane beam is positioned on a second longitudinal axis. Said second axis is perpendicular to the first axis. Said crane beam has a one end which is secured to the feeler pin. Said crane beam further has a second, opposite end. A measuring rod is positioned on a third longitudinal axis. Said third axis is substantially perpendicular to the second axis and is parallel to the first axis. Said measuring rod has a one end which is coupled to the second, opposite end of the crane beam. In this fashion, movement of the feeler pin is tracked by the measuring rod. Said rod further has a second end. An inductive control core is disposed upon the second end of the measuring rod for movement therewith. A stationary measuring coil has a hollow interior to receive therein the second end of the measuring rod which has the inductive core disposed thereon. In this fashion, the movement of the core in the coil is sensed. Finally, means is provided for electronically transmitting, amplifying and digitally displaying the movement of the measuring rod (having the inductive core disposed thereon) in the hollow interior of the stationary measuring coil.

Preferably, the measuring rod is comprised of ceramic and the control core is comprised of ferrite embedded in the ceramic. It is also preferred that the hollow interior of the measuring coil have a first diameter and that the control core disposed on the measuring rod have a second diameter which is substantially coincident to the first diameter for precisely receiving the control core within the hollow interior. It is further preferred that a coupling member be provided for elastically, rigidly securing the one end of the crane beam to the feeler pin.

In one embodiment, the crane beam includes a first section and a second section. Said sections are positioned substantially parallel to, and at least partially overlapping, one another. Said first section has a one end, which is secured to the feeler pin, and an opposite end. Said second section has a first end, which is secured to the opposite end of the first section, and a second opposite end which is coupled to the one end of the measuring rod. A resilient elastic ring is disposed over the opposite end of the first section and the first end of the second section. In this manner, the first section and the second section of the crane beam are resiliently secured to one another. Also, a bearing means braces the first and second sections against one another, whereby the said sections are maintained in a position being substantially parallel to, and at least partially overlapping, one another. Preferably, the bearing means is either a needle bearing or a pin bearing.

In a second embodiment, an attached ring has a one face which is oriented in an outwardly direction. Said ring is axially received on and carried by the measuring rod on the one end thereof. The crane beam further has a one face. Said one face of the crane beam is oriented facing in an outwardly direction which is opposite from the direction in which the one face of the attached ring is oriented. Also, an elastic U-shaped, inwardly-biased resilient elastic spring clamp is provided. Said spring clamp has a one end which is disposed inwardly-bearing against the one face of the attached ring. Said spring clamp further has a second end disposed inwardly-bearing against the one face of the crane beam. In this fashion, the measuring rod is resiliently coupled to the crane beam. Preferably, the one end of the measuring rod is rounded.

In a third embodiment, a spring steel band is provided. This band has a one end which is secured to the feeler pin. Said spring steel band further has a pair of parallel outwardly-extending, resilient arms which emerge from the one end thereof. Each of said arms has a second opposite end. A pair of bearings are provided. One of said bearings is disposed on a respective second opposite end of each respective arm. Said bearings are also oriented facing towards one another. Also, the one end of the measuring rod has formed thereon a pair of diametrically positioned recesses. In each of these recesses, a respective bearing is received. In this fashion, the one end of the measuring rod is resiliently secured to the second, opposite end of the crane beam. Preferably, the bearings disposed in the second opposite end of each arm is a pin bearing.

In a fourth embodiment, the crane beam is a circular closed resilient spring steel band. The one end of said band is secured to the feeler pin at a position thereon which is diametrical to the position where the second opposite end of said band is secured to the measuring rod. Preferably, the crane beam is secured to the feeler pin by a first screw. Also the crane beam is secured to the measuring rod by a second pin.

It is proposed to provide for a cardan or half-cardan coupling member between feeler pin and measuring rod which guarantees an exact drive of the measuring rod along the direction of the feeler pin and, besides, a free movement of the measuring rod. The measuring rod can then, on its part, be guided exactly into the middle of the measurement coil and the occurring mechanical faults can be taken up by the coupling member.

The exact guidance of the measuring rod with the control core in the measurement coil is, preferably, achieved by a construction of the hollow interior of the measurement coil so as to be an accurate linear guide for the measuring rod with control core which is formed precisely in diameter to the clearance of the linear guide. The unavoidable construction tolerances of the measuring gauge are therewith eliminated, and yet the movement of the feeler pin is transmitted accurately to the control core. Through the complete filling of the inner cross-section of the measurement coil by the control core, the efficiency of the measuring system is especially improved in that the magnetic gap is shortened. In this fashion, the electrical losses in the measuring transformer can be avoided. Through the exact guidance of the control core in the measurement coil, the measurement accuracy is likewise greatly enhanced because neither the turning play of the feeler pin nor position nor drive errors which result due to construction tolerances can exert an influence upon the position of the control core. Despite the minimum available space, a great linearity of the measuring system with exceptionally minimal tolerances can be achieved.

Particularly appropriate developments of the half-cardan coupling member between feeler pin and measuring rod appear under protection are also disclosed.

With reference to the figures, prototypes of the invention are further explained. In all of the figures, only the feeler pin, crane beam, coupling member, and measurement coil encompassing parts of the measuring gauge relevant to the invention are represented.

BRIEF DESCRIPTION OF THE DRAWINGS

FIG. 1 is a side view of the parts important to the invention of a first prototype.

FIG. 2 is a cross-section view taken along line II—II of FIG. 1.

FIG. 3 is a cross-section view taken along line III—III of FIG. 1.

DESCRIPTION OF PREFERRED EMBODIMENTS

Figure 4:
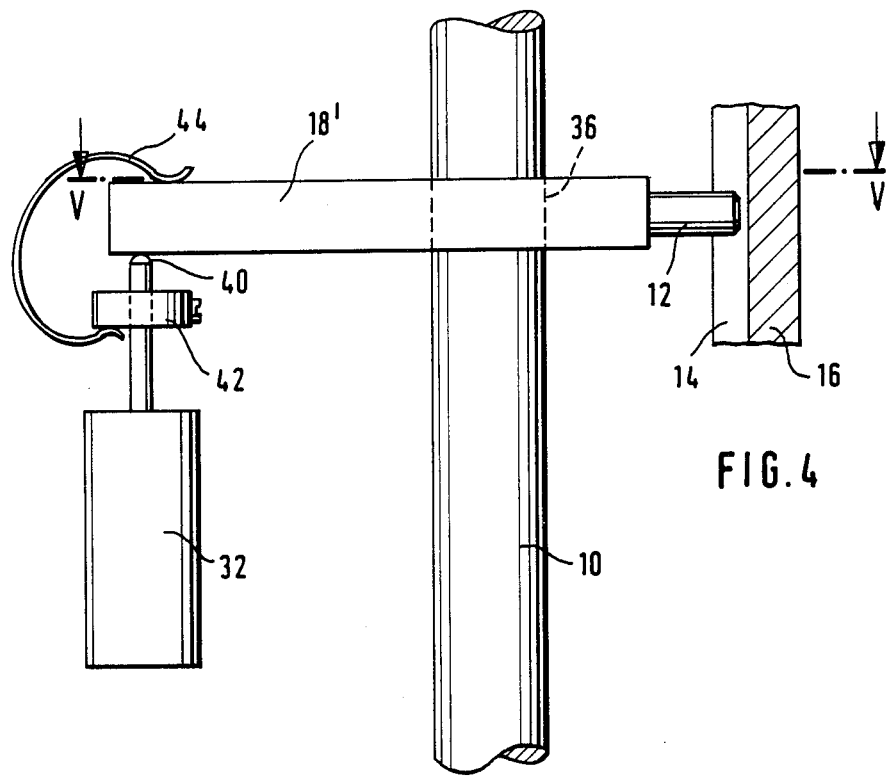
FIG. 4 is a side view of a second embodiment of the measuring gauge of the present invention.

The Rockwell-hardness tester and the method by which that tester works will be assumed to be known. Therefore, of the parts of the apparatus only a section of the feeler pin 10 under the measuring load will be presented. In the feeler pin 10 (which is positioned on a first, longitudinal axis), a security pin 12 is anchored projecting sideways which is guided in a sliding manner in a groove 14 of a guide track 16 running along the direction of the feeler pin. This results in a turn security (prevention of substantial rotational movement) of the feeler pin 10 with minimal play.

According to the invention, at another spot on the feeler pin a first section 18 a perpendicular crane beam is anchored, close to whose end a disc (bearing) 20 is attached which has a radial cutting (bearing) edge 22. On top of the cutting edge 22 lies a second section 24 of the crane beam which runs parallel to the first section 18 and which overlaps it. In the region of the overlap, both sections 18 and 24 of the crane beam are forcefully held together by means of an elastic (resilient) 0-ring 26.

At the outer end of the second section of the crane beam 24 a measuring rod 28 of ceramic material is attached near its end (on a third, longitudinal axis) in such a way so that it extends parallel to the feeler pin 10. The measuring rod penetrates through the hollow interior of a measurement coil 32 and carries in this region an inductive control core 34 formed, preferably, of a ferrite core. The measurement coil 32 and the core 34 comprise an electrical sensor or electrical sensing means 80. The hollow interior 30 is formed as an exact linear guide for the measuring rod 28, whereby the diameter of the measuring rod is fitted exactly to the inner diameter of the linear guide (hollow interior).

The electrical sensing means 80 is connected to an amplifier 82 by electrical connector 84. The amplifier 82 is connected to a digital display 86 by electrical connector 88.

The linear motion of the sensing rod 10 is transmitted exactly and without play to the control core (the core tracks the movement of the feeler pin) through the cutting edge, whereby eventually occurring play and construction tolerances are taken up by the half-cardan, elastic coupling members 20, 22, 26.

With the following embodiments, the same references for similar or corresponding parts are used as for the first embodiment.

Figure 5:
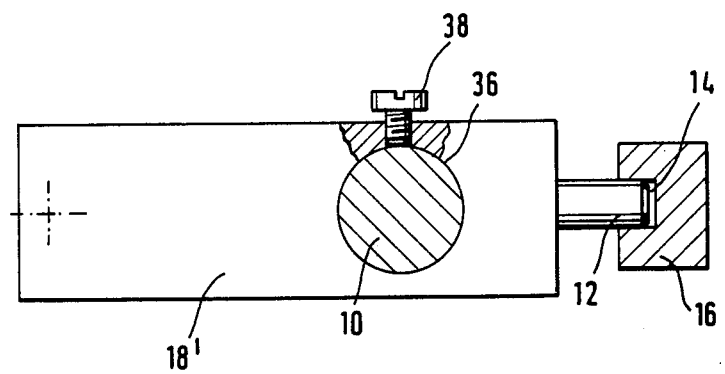
FIG. 5 is a cross-section view taken along line V—V of FIG. 4 in which the coupling clamp and the ring situated on the measuring rod have been omitted for the sake of clarity.

With the embodiment shown in FIGS. 4 and 5, the security pin is not directly fastened to the feeler pin 10 but extends integrally out of the end of a one-piece crane beam 18' (which is positioned on a second, longitudinal axis). The one end of crane beam 18' has a cross bore 36 formed therein, in which is received the feeler pin 10, where said pin 10 fixed (with the second axis being substantially perpendicular to the first axis) by means of a screw 38.

The second, opposite end of the crane beam 18' rests upon the rounded tip 40 at the one end of the measuring rod 28. The measurement coil 32 and the parts within are formed as in the embodiment shown in FIG. 1 on the second end of rod 28, and therefore need not again be presented here.

In the section lying outside (above) of the measurement coil 32, the one end of the measuring rod 28 carries an attached ring 42. An elastic U-shaped resiliently-biased clamp 44 has one end disposed inwardly-bearing against one face of the ring 42 and a second end inwardly-bearing against the one face of the crane beam, whereby clamp 44 holds the attached ring 42 and the crane beam 18' forcefully together.

Figures 6, 7:
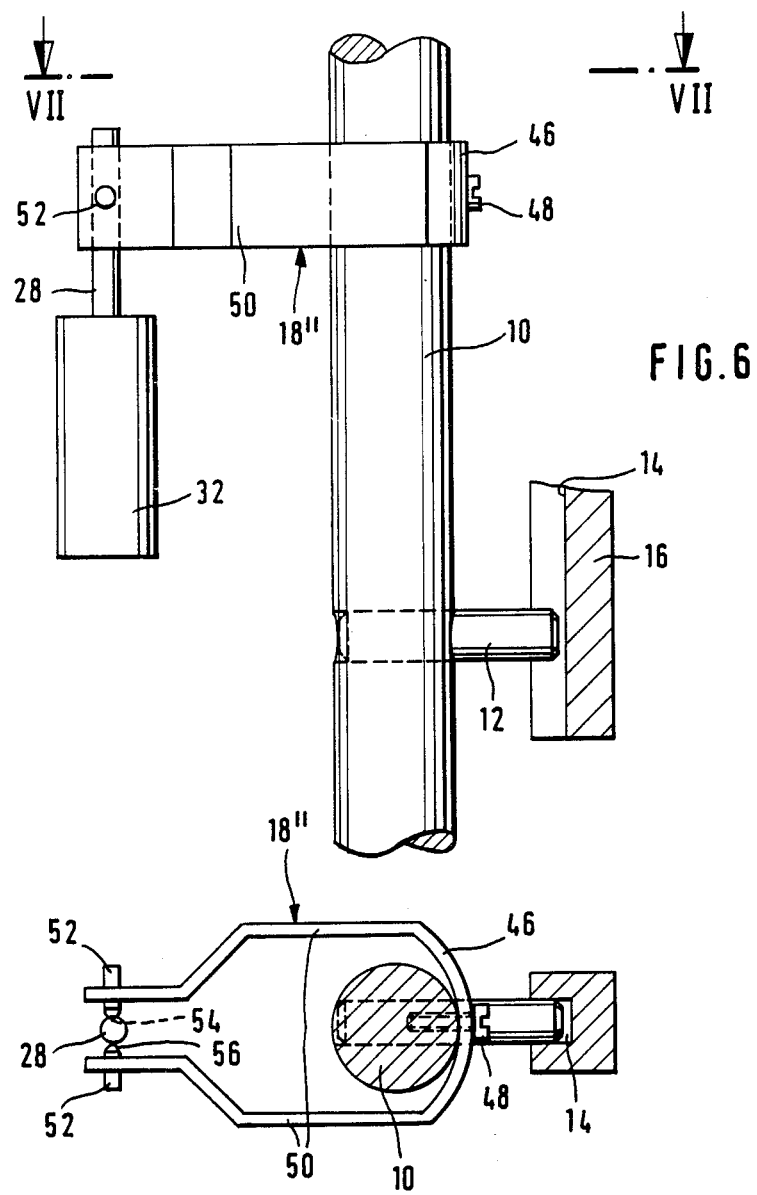
FIG. 6 is a side view of a third embodiment of the invention.
FIG. 7 is a cross-section view taken along the line VII—VII of FIG. 6.

Also in the embodiments shown in FIGS. 6 and 7 the crane beam 18'' is formed in one-piece as a band situated at the top of the feeler pin 10, made out of spring steel or material with similar bending characteristics. The spring steel band 18'' has at the side of the feeler pin 10 facing away from the measuring rod 28 a curved section (a one end) 46 whose curvature is somewhat less than the outside circumference of the feeler pin 10. The section 46 therefore only has a line-of-contact with the feeler pin 10 and is in this region fastened to the feeler pin 10 by means of a screw 48. Both of the arms 50 of the crane beam 18'' pointing towards the measuring rod 28, each carry near their opposing (second, opposite) ends a pin 52, each with a point 56 which are oriented towards one another that are received in a respective diametrically opposed depression (recess) 54 formed in the measuring rod 28 through the spring effect of the arms 50. Since the bending stiffness of the crane beam 18'' is very large perpendicular to the length of the feeler pin 10 attached at the upper edge of the length of the feeler pin 10, and since a forceful coupling of the arms 50 of the crane beam and the measuring rod 28 is accomplished through the penetration in the depression 54, there is produced during the movement of the feeler rod 10 along its length direction and unusually exact co-movement of the measuring rod 28. Moreover, eventual turning play of the feeler pin 10 as well as distance and drive error coming from construction tolerances is compensated for by means of the elastic coupling between the feeler pin 10 and the measuring rod 28 and, thus, are remain without influence upon the measurement.

Figure 8:
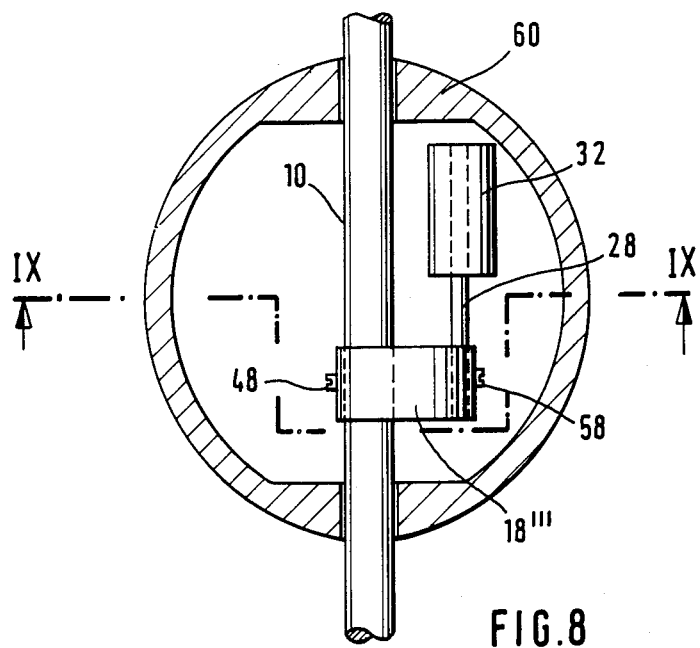
FIG. 8 is a view of a fourth embodiment of the measuring gauge of the present invention in which the housing of the measuring gauge is shown to illustrate positioning of the measuring gauge in the housing.
Figure 9:
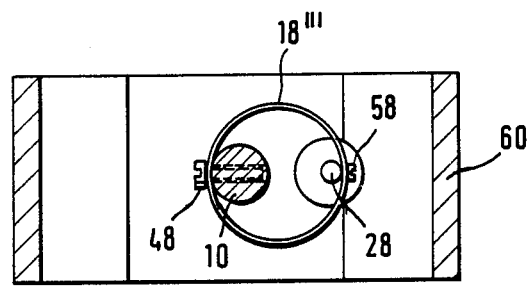
FIG. 9 is a cross-section view taken along line IX—IX of FIG. 8.

In the embodiment presented in smaller scale in FIGS. 8 and 9, a circular closed (resilient) spring steel band acting as a one-piece crane beam 18''' is provided which is similarly situated at the upper edge of the length of the feeler pin 10. It also is secured at its one end to the feeler pin 10 where it rests with linear contact on the sides of the feeler pin 10 and it is secured at its second, opposite (diametrically opposed) side to measuring rod 28, so that pin 10 and rod 28 are facing away from each other. In these positions, steel band is attached to the feeler pin 10 and measuring rod 28 by means of a screw 48 and 58. This embodiment is, as can be seen, primarily suited for the compensation of turning play and position tolerances for which drive errors cannot be compensated. During very exact guidance of the measuring rod 28, this is, however, not necessary so that the simplified embodiment suffices.

In addition, in FIGS. 8 and 9 is shown a housing 60 surrounding the entire measuring gauge with its parts relevant to the invention and the non-shown remaining parts of an electronic digital measuring gauge, whose dimensions corresponds to currently common and for this purpose widely used mechanical measuring gauges. The not-shown electronic parts of the measuring gauge are connected with the measurement coil 32 by known means. From this representation of the housing 60 it can be seen that at any time an existing mechanical measuring gauge can be replaced with an electronic measuring gauge according to the invention, whereby no additional demand upon space is created and the assembly expense remains limited. So at any time an existing hardness measuring apparatus can be retrofitted with an electronic measuring gauge according to the invention. The parts 12, 14, 16 for preventing turning of the feeler pin are not described in this prototype. Furthermore, it is to be remarked with this prototype that the measuring rod 28 stands up from the crane beam 18''' which easily would be equally possible in the other prototypes without influencing the effectiveness.

What is claimed is:

1. An electronic digital measuring gauge for a hardness tester comprising:
   a movable feeler pin;
   a movable tracking member;
   a resilient mechanical coupling means positioned between the feeler pin and the movable tracking member for securing the feeler pin and the movable tracking member, wherein the movable tracking member tracks the movement of the feeler pin;
   an electrical sensing means for electrically sensing the movement of the movable tracking member;

an amplifier for amplifying the electrically sensed movement of the tracking member;

means for electrically connecting the amplifier and the sensing means for conducting the electrically sensed movement of the tracking member from the electrical sensing means to the amplifier;

a digital display for digitally displaying the electrically sensed movement of the tracking member; and means for electrically connecting the amplifier and the digital display for conducting the electrically sensed movement from the amplifier to the digital display.

2. The electronic digital measuring gauge of claim 1, wherein the feeler pin and the tracking member are positioned on respective parallel longitudinal axes.

3. An electronic digital measuring gauge for a hardness tester comprising:

a housing;

a movable feeler pin positioned on a first longitudinal axis, said pin disposed through the housing and extending outwardly therefrom;

a crane beam positioned on a second longitudinal axis, said second axis being perpendicular to the first axis, said crane beam having a one end secured to the feeler pin, and further having a second, opposite end;

a measuring rod positioned on a third longitudinal axis, said third axis being substantially perpendicular to the second axis and parallel to the first axis, said measuring rod having a one end coupled to the second, opposite end of the crane beam, wherein movement of the feeler pin is tracked by the measuring rod, and said rod further having a second end;

an inductive control core disposed upon the second end of the measuring rod for movement therewith;

a stationary measuring coil having a hollow interior to receive therein the second end of the measuring rod having the inductive core disposed thereon, whereby the movement of the core in the coil is sensed; and means for electronically transmitting, amplifying and digitally displaying the sensed movement of the inductive control core in the hollow interior of the stationary measuring coil.

4. The measuring gauge of claim 3, wherein the measuring rod is comprised of ceramic, and further wherein the control core is comprised of ferrite embedded in the ceramic.

5. The measuring gauge of claim 3, further comprising a coupling member for elastically, rigidly securing the one end of the crane beam to the feeler pin.

6. The measuring gauge of claim 3, further comprising the hollow interior of the measuring coil having a first diameter and the control core disposed on the measuring rod having a second diameter being substantially coincident to the first diameter for precisely receiving the control core within the hollow interior.

7. The measuring gauge of claim 3, further comprising:

the crane beam including a first section and a second section, said sections positioned substantially parallel to and at least partially overlapping one another, said first section having a one end secured to the feeler pin and further having an opposite end, said second section having a first end secured to the opposite end of the first section, and further having a second opposite end coupled to the one end of the measuring rod;

a resilient elastic ring disposed over the opposite end of the first section and the first end of the second section, whereby the first section and the second section of the crane beam are resiliently secured to one another; and a bearing means for bracing the first and second sections against one another, whereby the said sections are maintained in a position being substantially parallel to, and at least partially overlapping one another.

8. The measuring device of claim 7, wherein the bearing means is a pin bearing.

9. The measuring device of claim 7, wherein the bearing means is a needle bearing.

10. The measuring device of claim 3, further comprising:

an attached ring having a one face oriented in an outwardly direction, said ring being axially received on and carried by the measuring rod on the one end thereof;

the crane beam further having a one face, said one face of the crane beam oriented facing in an outwardly direction being opposite from the direction in which the one face of the attached ring is oriented; and an elastic U-shaped, inwardly-biased resilient spring clamp, said spring clamp having a one end disposed inwardly-bearing against the one face of the attached ring, and said spring clamp further having a second end disposed inwardlybearing against the one face of the crane beam, whereby the measuring rod is resiliently coupled to the crane beam.

11. The measuring gauge of claim 10, wherein the one end of the measuring rod is rounded.

12. The measuring gauge of claim 3, wherein crane beam is comprised of:

a spring steel band having a one end secured to the feeler pin, said spring steel band further having a pair of parallel outwardly-extending, resilient arms emerging from the one end thereof, each of said arms having a second opposite end;

a pair of bearings, one of said bearings being disposed on a respective second opposite end of each respective arm, said bearings being oriented facing towards one another; and the one end of the measuring rod having formed thereon a pair of diametrically positioned recesses, whereby each of said bearings are received in a respective recess, resiliently securing the one end of the measuring rod to the second, opposite end of the crane beam.

13. The measuring gauge of claim 12, wherein the bearings disposed on the second opposite end of each side arm is a pin bearing.

14. The measuring device of claim 3, wherein the crane beam is comprised of a circular closed resilient spring steel band, and further wherein the one end of said band which is secured to the feeler pin at a position thereon being diametrical to the position where the second opposite end of said band is secured to the measuring rod.

15. The measuring device of claim 14, wherein the crane beam is secured to the feeler pin by a first screw, and wherein the crane beam is secured to the measuring rod by a second pin.

16. An electronic digital measuring gauge for a hardness tester comprising:
- a housing;
- a movable feeler pin positioned on a first longitudinal axis, said pin disposed through the housing and extending outwardly therefrom;
- a crane beam including a first section and a second section, each of said sections being positioned substantially parallel to and at least partially overlapping one another on separate, respective second longitudinal axes, each of said second axes being perpendicular to the first axis, said first section having a one end secured to the feeler pin and further having an opposite end, said second section having a first end secured to the opposite end of the first section, and further having a second opposite end;
- a resilient elastic ring disposed over the opposite end of the first section and the first end of the second section, whereby the first section and the second section of the crane beam are resiliently secured to one another;
- a bearing means for bracing the first and second sections against one another, whereby the said sections are maintained in a position being substantially parallel to, and at least partially overlapping one another;
- a measuring rod positioned on a third longitudinal axis, said third axis being substantially perpendicular to each of the respective second axes and parallel to the first axis, said measuring rod having a one end coupled to the second, opposite end of the second section of the crane beam, wherein movement of the feeler pin is tracked by the measuring rod, said rod further having a second end;
- an inductive control core disposed upon the second end of the measuring rod for movement therewith;
- a stationary measuring coil having a hollow interior to receive therein the second end of the measuring rod having the inductive core disposed thereon, whereby movement of the core in the coil is sensed; and
- means for electronically transmitting, amplifying and digitally displaying the sensed movement of the inductive core in the hollow interior of the stationary measuring coil.

17. The measuring gauge of claim 16, wherein the one end of the measuring rod is rounded.

18. An electronic digital measuring gauge for a hardness tester comprising:
- a housing;
- a movable feeler pin positioned on a first longitudinal axis, said pin disposed through the housing and extending outwardly therefrom;
- a crane beam positioned on a second longitudinal axis, said second axis being perpendicular to the first axis, said crane beam having a one end secured to the feeler pin, and further having a second, opposite end;
- a measuring rod positioned on a third longitudinal axis, said third axis being substantially perpendicular to the second axis and parallel to the first axis, said measuring rod having a one end and a second end;
- an attached ring having a one face oriented in an outwardly direction, said ring being axially received on and carried by the measuring rod on the one end thereof;
- the crane beam further having a one face, said one face of the crane beam oriented facing in an outwardly direction being opposite from the direction in which the one face of the attached ring is oriented;
- an elastic U-shaped, inwardly-biased resilient spring clamp, said spring clamp having a one end disposed inwardly-bearing against the one face of the attached ring, and said spring clamp further having a second end disposed inwardly-bearing against the one face of the crane beam, whereby the measuring rod is resiliently coupled to the crane beam, so that movement of the feeler pin is tracked by the measuring rod;
- an inductive control core disposed upon the second end of the measuring rod for movement therewith;
- a stationary measuring coil having a hollow interior to receive therein the second end of the measuring rod having the inductive core disposed thereon, whereby movement of the core in the coil is sensed; and
- means for electronically transmitting, amplifying and digitally displaying the sensed movement of the inductive core in the hollow interior of the stationary measuring coil.

19. An electronic digital measuring gauge for a hardness tester comprising:
- a housing;
- a movable feeler pin positioned on a first longitudinal axis, said pin disposed through the housing and extending outwardly therefrom;
- a crane beam positioned on a second longitudinal axis, said second axis being perpendicular to the first axis, said crane beam including a spring steel band having a one end secured to the feeler pin, said spring steel band further having a pair of parallel outwardly-extending, resilient arms emerging from the one end thereof, each of said arms having a second opposite end;
- a pair of bearings, one of said bearings being disposed on a respective second, opposite end of each respective arm, said bearings being oriented facing towards one another;
- a measuring rod positioned on a third longitudinal axis, said third axis being substantially perpendicular to the second axis and parallel to the first axis, said measuring rod having a one end and a second end, said one end of the measuring rod having formed thereon a pair of diametrically positioned recesses, whereby each of said bearings are received in a respective recess, resiliently coupling the one end of the measuring rod to the second, opposite end of the crane beam, wherein movement of the feeler pin is tracked by the measuring rod;
- an inductive control core disposed upon the second end of the measuring rod for movement therewith;
- a stationary measuring coil having a hollow interior to receive therein the second end of he measuring rod having the inductive core disposed thereon, whereby movement of the core in the coil is sensed; and
- means for electronically transmitting, amplifying and digitally displaying the sensed movement of the inductive core in the hollow interior of the stationary measuring coil.

20. The measuring gauge of claim 19, wherein the bearings disposed on the second opposite end of each side arm is a pin bearing.

21. An electronic digital measuring gauge for a hardness tester comprising:

- a housing;
- a movable feeler pin positioned on a first longitudinal axis, said pin disposed through the housing and extending outwardly therefrom;
- a crane beam positioned on a second longitudinal axis, said second axis being perpendicular to the first axis, said crane beam including a circular, closed resilient spring steel band, having a one end and a second opposite end, further wherein the one end of said band is secured to the feeler pin at a position thereon being diametrical to the position where the second opposite end of said band is resiliently secured to the measuring rod;
- a measuring rod positioned on a third longitudinal axis, said third axis being substantially perpendicular to the second axis and parallel to the first axis, said measuring rod having a one end coupled to the second, opposite end of the crane beam, wherein movement of the feeler pin is tracked by the measuring rod, and said rod further having a second end;
- an inductive control core disposed upon the second end of the measuring rod for movement therewith;
- a stationary measuring coil having a hollow interior to receive therein the second end of the measuring rod having the inductive core disposed thereon, whereby movement of the core in the coil is sensed; and
- means for electronically transmitting, amplifying and digitally displaying the sensed movement of the inductive core in the hollow interior of the stationary measuring coil.

22. The measuring device of claim 21, wherein the crane beam is secured to the feeler pin by a first screw, and wherein the crane beam is secured to the measuring rod by a second pin.

* * * * *